United States Patent
Rao et al.

(10) Patent No.: US 9,850,366 B2
(45) Date of Patent: Dec. 26, 2017

(54) EPDXIDIZED FATTY ACID ALKYL ESTER PLASTICIZERS AND METHODS FOR MAKING EPDXIDIZED FATTY ACID ALKYL ESTER PLASTICIZERS

(71) Applicant: Dow Global Technologies LLC, Midland, MI (US)

(72) Inventors: Neeta Rao, Pune (IN); Saurabh Kaujalgikar, Pune (IN); Bharat I. Chaudhary, Princeton, NJ (US); Shreyas Bhide, Mumbai (IN); Shantaram Morye, Pune (IN); Sachin Agashe, Pune (IN)

(73) Assignee: Dow Global Technologies LLC, Midland, MI (US)

( * ) Notice: Subject to any disclaimer, the term of this patent is extended or adjusted under 35 U.S.C. 154(b) by 277 days.

(21) Appl. No.: 14/423,653

(22) PCT Filed: Oct. 18, 2012

(86) PCT No.: PCT/IN2012/000688
§ 371 (c)(1),
(2) Date: Feb. 24, 2015

(87) PCT Pub. No.: WO2014/061026
PCT Pub. Date: Apr. 24, 2014

(65) Prior Publication Data
US 2015/0240050 A1    Aug. 27, 2015

(51) Int. Cl.
*C07C 51/00* (2006.01)
*C08K 5/1515* (2006.01)
(Continued)

(52) U.S. Cl.
CPC .......... *C08K 5/1515* (2013.01); *C07D 301/12* (2013.01); *C08K 5/0016* (2013.01); *Y10T 428/139* (2015.01); *Y10T 428/1334* (2015.01)

(58) Field of Classification Search
CPC ..... C08K 5/515; C08K 5/0016; C07D 301/12
(Continued)

(56) References Cited

U.S. PATENT DOCUMENTS 2,397,592 A    4/1946  Blades
2,403,215 A    7/1946  Foster
(Continued)

FOREIGN PATENT DOCUMENTS

CA    1188445 A1    6/1985
CN    101591588 A   12/2009
(Continued)

OTHER PUBLICATIONS

Barnicoat, C.R. 1945. Reactions and properties of annatto as a cheese colour. Part II. J. Dairy Res. 14: 59-63.
(Continued)

*Primary Examiner* — Deborah D Carr

(57) ABSTRACT

Epoxidized fatty acid alkyl ester and methods for making epoxidized fatty acid alkyl ester. The epoxidized fatty acid alkyl ester is prepared from a fatty acid alkyl ester starting material comprising at least one of mono-unsaturated and di-unsaturated fatty acid alkyl ester molecules in a combined amount of at least 85 weight percent. Such epoxidized fatty acid alkyl esters can be employed in plasticizer compositions, either alone or in combination with other plasticizers, such as epoxidized natural oils. Such plasticizers in turn may be used in the formation of polymeric compositions.

9 Claims, 1 Drawing Sheet

(51) Int. Cl.
*C08K 5/00* (2006.01)
*C07D 301/12* (2006.01)

(58) Field of Classification Search
USPC .................................................... 554/149
See application file for complete search history.

(56) References Cited

U.S. PATENT DOCUMENTS

| | | | |
|---|---|---|---|
| 2,458,484 A | 1/1949 | Terry et al. | |
| 2,500,918 A | 3/1950 | Rueter et al. | |
| 2,618,622 A | 11/1952 | Grummit et al. | |
| 2,666,752 A | 1/1954 | Grummit et al. | |
| 3,138,566 A | 6/1964 | Arnold | |
| 3,381,837 A | 5/1968 | Testa et al. | |
| 3,409,580 A | 11/1968 | Alzner | |
| 3,451,958 A | 6/1969 | Riedeman et al. | |
| 3,639,318 A | 2/1972 | Tijunelis et al. | |
| 3,668,091 A | 6/1972 | French et al. | |
| 3,712,875 A | 1/1973 | Tijunelis | |
| 3,778,465 A | 12/1973 | Barnstorf | |
| 3,780,140 A | 12/1973 | Hammer | |
| 3,868,341 A | 2/1975 | Sauer et al. | |
| 3,872,187 A | 3/1975 | Fath | |
| 3,891,694 A | 6/1975 | Mills et al. | |
| 4,083,816 A | 4/1978 | Frankel et al. | |
| 4,346,145 A | 8/1982 | Choi et al. | |
| 4,421,886 A | 12/1983 | Worschech et al. | |
| 4,426,477 A | 1/1984 | Yasumatsu et al. | |
| 4,556,694 A | 12/1985 | Wallace | |
| 4,605,694 A | 8/1986 | Walker | |
| 4,612,192 A | 9/1986 | Scheuffgen et al. | |
| 4,613,533 A | 9/1986 | Loomis et al. | |
| 4,627,993 A | 12/1986 | Loomis | |
| 4,670,494 A | 6/1987 | Semenza, Jr. | |
| 4,857,600 A | 8/1989 | Gross et al. | |
| 5,225,108 A | 7/1993 | Bae et al. | |
| 5,227,417 A | 7/1993 | Kroushl, III | |
| 5,246,783 A | 9/1993 | Spenadel et al. | |
| 5,270,366 A | 12/1993 | Hein | |
| 5,278,236 A | 1/1994 | Case et al. | |
| 5,430,108 A | 7/1995 | Schlosberg et al. | |
| 5,454,806 A | 10/1995 | Shinonome | |
| 5,464,903 A | 11/1995 | Hofmann | |
| 5,466,267 A | 11/1995 | Baillargeon et al. | |
| 5,575,965 A | 11/1996 | Caronia et al. | |
| 5,736,605 A | 4/1998 | Oshima | |
| 5,756,570 A | 5/1998 | Hoch et al. | |
| 5,886,072 A | 3/1999 | Linsky et al. | |
| 6,063,846 A | 5/2000 | Weng et al. | |
| 6,114,425 A | 9/2000 | Day et al. | |
| 6,274,750 B1 | 8/2001 | Sato et al. | |
| 6,417,260 B1 | 7/2002 | Weng et al. | |
| 6,437,170 B1 | 8/2002 | Thil et al. | |
| 6,451,958 B1 | 9/2002 | Fan et al. | |
| 6,495,033 B1 | 12/2002 | Talboom | |
| 6,496,629 B2 | 12/2002 | Ma et al. | |
| 6,608,142 B1 | 8/2003 | Weng et al. | |
| 6,706,815 B2 | 3/2004 | Marchand et al. | |
| 6,714,707 B2 | 3/2004 | Rossi et al. | |
| 6,734,241 B1 | 5/2004 | Nielsen et al. | |
| 6,797,753 B2 | 9/2004 | Benecke et al. | |
| 6,849,694 B2 | 2/2005 | Hata | |
| 6,949,597 B2 | 9/2005 | Nielsen et al. | |
| 7,700,675 B2 | 4/2010 | Bueno de Almeida et al. | |
| 2002/0013396 A1* | 1/2002 | Benecke | C08K 5/0016 524/315 |
| 2004/0122159 A1 | 6/2004 | Mhetar et al. | |
| 2005/0090590 A1 | 4/2005 | Nielsen et al. | |
| 2005/0203230 A1 | 9/2005 | Kadakia et al. | |
| 2006/0025544 A1 | 2/2006 | Koube et al. | |
| 2006/0276575 A1 | 12/2006 | Hamaguchi et al. | |
| 2007/0100049 A1 | 5/2007 | Ishizuka | |
| 2007/0135562 A1 | 6/2007 | Freese et al. | |
| 2008/0200595 A1 | 8/2008 | Hinault et al. | |
| 2008/0227993 A1 | 9/2008 | Zuckerman | |
| 2009/0149585 A1 | 6/2009 | De Quadros Junior et al. | |
| 2009/0149586 A1 | 6/2009 | De Quadros Junior et al. | |
| 2009/0306257 A1* | 12/2009 | Wehner | C08L 27/06 524/100 |
| 2009/0312478 A1 | 12/2009 | Hasegawa et al. | |
| 2010/0010127 A1 | 1/2010 | Barki et al. | |
| 2010/0256278 A1 | 10/2010 | Harada et al. | |
| 2011/0076502 A1 | 3/2011 | Chaudhary et al. | |
| 2011/0272174 A1 | 11/2011 | Chaudhary | |
| 2013/0005937 A1 | 1/2013 | Cramail et al. | |

FOREIGN PATENT DOCUMENTS

| | | | |
|---|---|---|---|
| CN | 101824193 A | 9/2010 | |
| CN | 101914219 A | 12/2010 | |
| EP | 0192961 A1 | 9/1986 | |
| EP | 0358179 A2 | 3/1990 | |
| EP | 0364717 A1 | 4/1990 | |
| EP | 0 393 813 A1 | 10/1990 | |
| EP | 0473915 A1 | 3/1992 | |
| EP | 0565984 A1 | 10/1993 | |
| EP | 0986606 A1 | 3/2000 | |
| EP | 1218443 A1 | 7/2002 | |
| EP | 1361039 A1 | 11/2003 | |
| EP | 1624014 A1 | 2/2006 | |
| EP | 2070977 A2 | 6/2009 | |
| EP | 2245089 A1 | 11/2010 | |
| FR | 1437722 A | 5/1966 | |
| GB | 102292 A | 11/1916 | |
| GB | 499931 A | 1/1939 | |
| GB | 790314 A | 2/1958 | |
| GB | 805252 A * | 12/1958 | ........... C08K 5/1515 |
| GB | 910543 A | 11/1962 | |
| GB | 934689 A | 8/1963 | |
| GB | 1102506 A | 2/1968 | |
| GB | 1341623 A | 12/1973 | |
| GB | 2155021 A | 9/1985 | |
| JP | S44-007131 | 3/1969 | |
| JP | S61-016950 | 1/1986 | |
| JP | 04-059851 B2 | 2/1992 | |
| JP | H04-085354 | 3/1992 | |
| JP | H04-261452 A | 9/1992 | |
| JP | 2000-319468 A | 11/2000 | |
| JP | 2003-064233 A | 3/2003 | |
| JP | 2003-297149 A | 10/2003 | |
| JP | 2004311064 A | 11/2004 | |
| JP | 2010-042669 A | 2/2010 | |
| WO | 1997030115 A1 | 8/1997 | |
| WO | 0114466 A1 | 3/2001 | |
| WO | 2001098404 A2 | 12/2001 | |
| WO | 2004052977 A1 | 6/2004 | |
| WO | 2007006489 A1 | 1/2007 | |
| WO | 2008081330 A1 | 7/2008 | |
| WO | 2008081332 A1 | 7/2008 | |
| WO | 2008122364 A1 | 10/2008 | |
| WO | 2009102877 A1 | 8/2009 | |
| WO | 2011041380 A1 | 4/2011 | |
| WO | 2011041388 A1 | 4/2011 | |
| WO | 2011041372 A1 | 4/2011 | |
| WO | 2012130545 A1 | 10/2012 | |
| WO | 2013003225 A2 | 1/2013 | |

OTHER PUBLICATIONS

Bizzari, S.N. et al (2003), Plasticizers. CEH Marketing Research Report, 38-64, Retrieved from http://www.sriconsulting.com.

Campanella A. et al.; High Yield Epoxidation of Fatty Acid Methyl Esters with Performic Acid Generated In Situ; Chemical Engineering Journal, 144 (2008) 466-475 (Elsevier B.V.).

Chuanshang Cai, et al.; Studies on the Kinetics of In Situ Epoxidation of Vegetable Oils; Eur. J. Lipid Sci. Technol., 2008, 110, 341-346 (Wiley-VCH GmbH & Co. KGaA, Weinheim).

Corrigan, Brian Oil purification, filtration and reclamation, Iron Age (1947) 159(14).

Danisco, Grindsted Soft-n-Safe brochure (date unknown).

Du G., et al., Catalytic Epoxidation of Methyl Linoleate, JAOCS, vol. 81, No. 4 (2004).

(56) References Cited

OTHER PUBLICATIONS

Freedman, F., Butterfield, R., and Pryde, E.H. Transesterification Kinetics of Soybean Oil. JAOCS, 63(10) p. 1375 (1986).
Gan, L. H., et al (1994) Epozidized esters of palm olein as plasticizers for poly (vinyl chloride). European Polymer Journal, 31(8), 719-724.
Greenspan, F. P. et al (1953) Epoxy fatty acid ester plasticizers. Indstrial and Engineering Chemistry, 445(12), 2722-2726.
Greenspan, F.P. et al (1956), Epoxy fatty acid ester plasticizers. Preparartion and properties, The Journal of the American Oil Chemists Society, 33, 391-394.
Grummitt O. and Fleming H. Acetylated Castor Oil Industrial and Engineering Chemistry, vol. 37, No. 5, May 1945, pp. 485-491.
Haas, Michael J. Improving the Economics of biodiesel production through the use of low value lipids as feedstocks: vegetable oil soapstock, Fuel Processing Technology 86 p. 1087-96 (2005).
Jensen, R.G. Purification of Triglycerides with an Aluminca Column, Lipids, 451-452 (1966).
Morgenstern, B. "Epoxidized Fatty Acid Esters as Plasticizers for PVC" dated Apr. 22, 2005.
Morgenstern, B. Epoxidized Fatty Acid Esters as Plasticizers for PVC, presented at the 7th Freiberg Polymer Conference, Apr. 21 and 22, 2005.
Morgenstern, B. Use of Modified Fatty Acid Esters as Plasticizers for PVC, dated Sep. 12, 2003.
Opposition to patent EP2245089, dated Jan. 9, 2013.
Orellana-Coca et al., Lipase Mediated Simultaneious Esterification and Epoxidation of Oleic Acid for the Production of Alkylepoxystearates. Journal of Molecular Catalysis B: Enzymatic 44 (2007) 133-137.
Stuart, A et al., Polym. Bull. (2010) 65:589-598.
Rehberg, C. et. Al. Plasticizers from Lactic Esters and Biabasic Acids Ind. Eng. Chem., 1952, 44 (9), pp. 2191-2195.
Santacesaria E. et al.; A Biphasic Model Describing Soybean Oil Epoxidation with H2O2 in a Fed-Batch Reactor; Chemical Engineering Journal, vol. 173, Issue 1, Sep. 1, 2011, pp. 198-209 (Elsevier B.V.).
Senžana S. et al.; Kinetics of In Situ Epoxidation of Soybean Oil in Bulk Catalyzed by Ion Exchange Resin; Journal of the American Oil Chemists' Society, vol. 78, No. 7 (2001) 725-731 (AOCS Press).
Sheehan, J et al. "A Look Back at the U.S. Department of Energy's Aquatic Species Program: Biodiesel from Algae", National Renewable Energy Laboratory, Colorado, Jul. 1998, pp. 1-294.
Taylor, D. R. Proceedings of the World Conference on oilseed technology and utilization, Adsorptive Purification, American Oil Chemists Society, Champaing, 1992, p. 152-165.
Tekin A., and Hammond E. Factors Affecting the Electrical Resistivity of Soybean Oil, JAOCS, vol. 75(6) 1998.
XP002657062 Vertellus Performance Materials Inc.; Flexricin P-8 Technical Data Sheet, Nov. 2006.
XP002669860, Thomson Scientific, Mar. 13, 2009, London, GB.
Erythropel H. C. et al; "Designing green plasticizers: Influence of molecular geometry on biodegradation and plasticization properties", Chemosphere, Pergamon Press, Oxford, GB, vol. 86, No. 8, Nov. 21, 2011, pp. 759-766.
Kastner J. et al; Aqueous leaching of di-2-ethylhexyl phthalate and green plasticizers from poly(vinyl chloride), Science of the Total Enviornment, Elsevier, Amsterdam, NL, vol. 432, Jun. 5, 2012, pp. 357-364.
XP002696108, Tables 2-6, Jun. 10, 2006; Retrieved from the Internet. URL: www.fao.org/es/esn/food/bio-10t.pdf.
http://hebjingu.en.alibaba.com/.
http://en.wikipedia.org/wiki/Chlorine.
http://en.wikipedia.org/wiki/Bleaching_of_wood_pulp.
TCI America, Online Catalog: Tributyrin; http://web.archive.org/web/20080511154307/http://www.tciamerica.com/.
PCT/US2009/033935, International Preliminary Report on Patentability, dated Aug. 26, 2010.
PCT/US2009/033935 International Search Report and Written Opinion, dated May 18, 2009.
PCT/US2010/050654 International Search Report and Written Opinion dated Nov. 9, 2010.
PCT/US2010/050676 International Search Report and Written Opinion dated Jan. 12, 2011.
PCT/US2010/050690 International Preliminary Report on Patentability, dated Jan. 12, 2012.
PCT/US2010/050690 International Search Report and Written Opinion, dated Aug. 2, 2011.
PCT/US2010/050699 International Search Report and Written Opinion, dated Nov. 8, 2010.
PCT/US2011/035143 International Search Report and Written Opinion, dated Aug. 26, 2011.
PCT/US2011/041557 International Preliminary Report on Patentability, dated Aug. 31, 2012.
PCT/US2011/041557 International Search Report and Written Opinion dated Sep. 5, 2011.
PCT/US2011/045653 International Search Report and Written Opinion, dated Oct. 7, 2011.
PCT/US2012/043740 International Search Report and Written Opinion, dated Jan. 23, 2013.
PCT/US2012/055070 International Search Report and Written Opinion, dated Dec. 3, 2012.
PCT/US2013/023362 International Search Report and Written Opinion, dated Mar. 28, 2013.
PCT/US2013/023362, International Preliminary Report on Patentability, dated Aug. 12, 2014.
PCT/US2011/059166 International Search Report and Written Opinion, dated Feb. 29, 2012.
PCT/US2011/059166, International Preliminary Report on Patentability, dated May 7, 2013.
PCT/IN2012/000745 International Search Report and Written Opinion, dated Aug. 29, 2013.
PCT/IN2012/000745 International Preliminary Report on Patentability, dated May 12, 2015.
PCT/US2013/039841, International Search Report and Written Opinion, dated Mar. 27, 2014.
PCT/IN2012/00688, International Search Report and Written Opinion, dated Jun. 18, 2013.
PCT/IN2012/00688, International Preliminary Report on Patentability, dated Apr. 30, 2015.
PCT/IN2012/000746 International Search Report and Written Opinion, dated May 31, 2013.
PCT/IN2012/000746, International Preliminary Report on Patentability, dated May 12, 2015.
PCT/US2013/039840 International Search Report and Written Opinion, dated Jul. 11, 2013.
PCT/US2013/039840, International Preliminary Report on Patentability, dated Dec. 31, 2014.
PCT/US2014/020556 International Search Report and Written Opinion, dated Jun. 25, 2014.
PCT/US2010/050654, International Preliminary Report on Patentability, dated Mar. 31, 2012.
PCT/US2010/050676, International Preliminary Report on Patentability, dated Mar. 31, 2012.
PCT/US2011/045653, International Preliminary Report on Patentability, dated Jan. 28, 2013.
PCT/US2012/043740, International Preliminary Report on Patentability, dated Jan. 7, 2014.
PCT/US2012/055070, International Preliminary Report on Patentability, dated Apr. 1, 2014.
PCT/US2010/050669, International Preliminary Report on Patentability, dated Apr. 11, 2012.
PCT/US2011/035143, International Preliminary Report on Patentability, dated Nov. 10, 2012.
PCT/US2013/039841, International Preliminary Report on Patentability, dated Dec. 21, 2014.

* cited by examiner

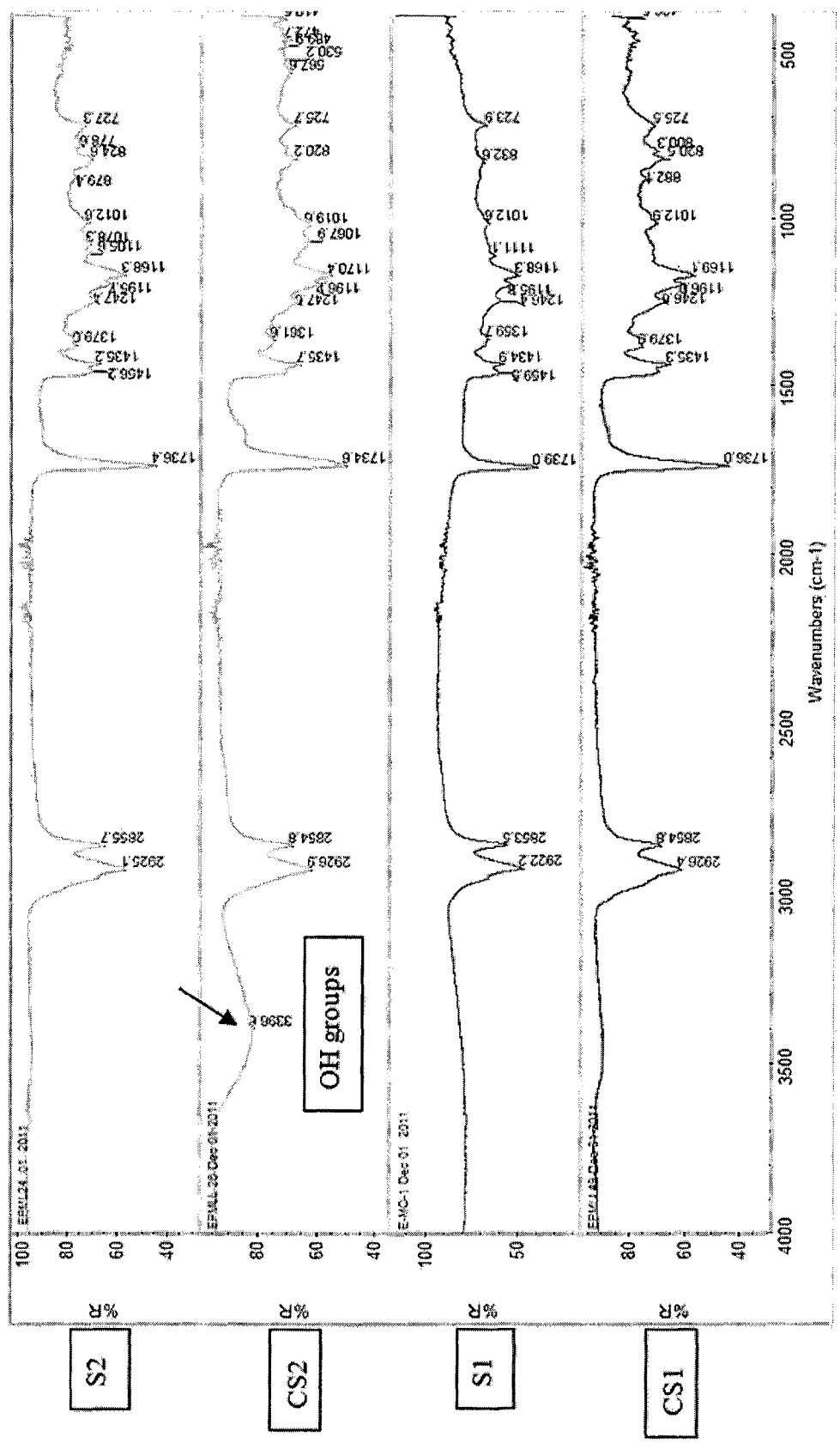

EPDXIDIZED FATTY ACID ALKYL ESTER PLASTICIZERS AND METHODS FOR MAKING EPDXIDIZED FATTY ACID ALKYL ESTER PLASTICIZERS

FIELD

Various embodiments of the present invention relate to epoxidized fatty acid alkyl ester plasticizers and plasticized polymeric compositions.

INTRODUCTION

Plasticizers are compounds or mixtures of compounds that, when added to a polymer resin, can lower the modulus and tensile strength, and increase flexibility, elongation, impact strength, and tear strength of the resin (typically a thermoplastic polymer) to which they are added. A plasticizer may also lower the glass transition temperature of the polymer resin, which enhances processability of the polymer resin.

Phthalic acid diesters (also known as "phthalates") are commonly used as plasticizers in many flexible polymer products, such as polymer products formed from polyvinyl chloride ("PVC") and other vinyl polymers. Examples of phthalate plasticizers include diisononyl phthalate, diallyl phthalate, di-2-ethylhexyl-phthalate, dioctyl phthalate, and diisodecyl phthalate.

Phthalate plasticizers have recently come under intense scrutiny by public interest groups concerned about the negative environmental impact of phthalates and potential adverse health effects in humans exposed to phthalates. Accordingly, suitable replacements for phthalate plasticizers are desired.

SUMMARY

One embodiment is a process for making a plasticizer, said process comprising: epoxidizing a fatty acid alkyl ester, thereby producing an epoxidized fatty acid alkyl ester, wherein said fatty acid alkyl ester comprises at least one of mono-unsaturated fatty acid alkyl ester molecules and di-unsaturated fatty acid alkyl ester molecules in a combined amount of at least 85 weight percent, based on the total weight of said fatty acid alkyl ester.

BRIEF DESCRIPTION OF THE DRAWINGS

FIG. 1 presents four infrared spectra of two samples and two comparative samples of epoxidized fatty acid methyl esters prepared in Example 1.

DETAILED DESCRIPTION

Various embodiments of the present invention concern plasticizers comprising an epoxidized fatty acid alkyl ester. The plasticizers may additionally include an epoxidized natural oil. Such plasticizers can be incorporated with a polymeric resin to form plasticized polymeric compositions, which can in turn be employed in various articles of manufacture.

Plasticizer

The present disclosure provides a plasticizer comprising an epoxidized fatty acid alkyl ester. The epoxidized fatty acid alkyl ester is prepared by epoxidizing a fatty acid alkyl ester. Generally, the fatty acid alkyl ester is composed of saturated fatty acid alkyl ester molecules, mono-unsaturated fatty acid alkyl ester molecules, di-unsaturated fatty acid alkyl ester molecules, and polyunsaturated fatty acid alkyl ester molecules (i.e., fatty acid alkyl ester molecules having three or more carbon-carbon double bonds). When referring to unsaturation of the fatty acid alkyl ester molecules herein, it is intended to denote unsaturation located on the fatty acid carbon chain of the fatty acid alkyl ester molecule, and excludes consideration of possible unsaturation on the alkyl moiety of the fatty acid alkyl ester molecule.

In one or more embodiments, the fatty acid alkyl ester starting material comprises at least one of mono-unsaturated and di-unsaturated fatty acid alkyl ester molecules in a combined amount of at least 85, at least 90, at least 95, or at least 99 weight percent ("wt %") based on the entire fatty acid alkyl ester weight. In various embodiments, mono-unsaturated fatty acid alkyl ester molecules can constitute in the range of from 10 to 60 wt %, 15 to 50 wt %, 20 to 40 wt %, or 25 to 30 wt % of the fatty acid alkyl ester based on the entire fatty acid alkyl ester weight. Additionally, di-unsaturated fatty acid alkyl ester molecules can constitute in the range of from 40 to 90 wt %, 45 to 85 wt %, from 50 to 75 wt %, or 55 to 65 wt % of the fatty acid alkyl ester based on the entire fatty acid alkyl ester weight.

In one or more embodiments, the fatty acid alkyl ester comprises polyunsaturated fatty acid alkyl ester molecules in an amount of less than 5, less than 4, less than 3, less than 2, or less than 1 wt % based on the total fatty acid alkyl ester weight. In various embodiments, the fatty acid alkyl ester can be free or substantially free of polyunsaturated fatty acid alkyl ester molecules. As used herein, the phrase "substantially free" denotes a concentration of less than 10 parts per million by weight.

In one or more embodiments, the fatty acid alkyl ester comprises saturated fatty acid alkyl ester molecules in an amount of less than 14, less than 12, less than 10 or less than 8 wt %, based on the entire weight of the fatty acid alkyl ester. In various embodiments, the fatty acid alkyl ester can be free or substantially free of saturated fatty acid alkyl ester molecules.

In each of the foregoing embodiments, the fatty acid alkyl ester's composition can be ascertained by gas chromatography ("GC"). For example, GC analysis can be performed using an Agilent 7890 A GC instrument with flame ionization detector. Approx 10 mg of a sample can be diluted to 1 mL of the methanol and 0.1 µL can be injected on a J&W 123-1111, 15 m, 320 micron, 0.1 micron column. Flow rate can be 13.85 mL/min, maintained at 30 psi with hold time of 10.3. Initial pressure can be 10 psi with a hold time of 1 minute, increased to 20 psi at a rate of 20 psi/min with a hold time of 12.5 minutes. Injector temperature can be 350° C. with a split ratio was 30:1. Initial temperature can be 60° C. with a hold time of 1 minute, increased to 390° C. with a hold time of 2 minutes. Detector temperature can be 400° C.

The alkyl group of the fatty acid alkyl ester is not particularly limited. In various embodiments, the alkyl group of the fatty acid alkyl ester is selected from the group consisting of saturated or unsaturated, branched or straight-chain $C_1$ to $C_4$ (i.e., having from 1 to 4 carbon atoms) alkyl groups. As used herein the term "alkyl" denotes a univalent group formed by removing a hydrogen atom from a hydrocarbon. In various embodiments, the alkyl group is saturated and straight-chain. Non-limiting examples of suitable alkyl groups include methyl, ethyl, 1-propyl, 2-propyl, 1-butyl, isobutyl, t-butyl, or combinations of two or more thereof. In an embodiment, the alkyl group of the fatty acid alkyl ester is methyl. Accordingly, in various embodiments, the fatty acid alkyl ester is a fatty acid methyl ester ("FAME").

The length of the fatty acid carbon chain of the fatty acid alkyl ester is not particularly limited. In various embodiments, the length of the fatty acid carbon chain can be from 10 to 24 carbon atoms, from 12 to 20 carbon atoms, or from 12 to 18 carbon atoms long. When referring to the number of carbon atoms in the fatty acid chain, the carbonyl carbon of the fatty acid is intended to be included. For instance, a fatty acid having 18 carbon atoms is stearic acid. In an embodiment, the fatty acid alkyl ester has a carbon chain length of 18 carbon atoms. In various embodiments, fatty acid alkyl ester molecules having a carbon chain length of 18 carbon atoms can constitute at least 50, at least 60, at least 70, at least 80, at least 90, at least 99, all or substantially all of the fatty acid alkyl ester.

In various embodiments, the above-mentioned mono-unsaturated fatty acid alkyl ester comprises alkyl oleate (e.g., methyl oleate). In one or more embodiments, the above-mentioned di-unsaturated fatty acid alkyl ester comprises alkyl linoleate (e.g., methyl linoleate). In some embodiments, the above-mentioned poly-unsaturated fatty acid alkyl ester comprises alkyl linolenate (e.g., methyl linolenate). In an embodiment, the above-mentioned saturated fatty acid alkyl ester comprises alkyl stearate (e.g., methyl stearate).

The above-described fatty acid alkyl ester can be prepared using any known or hereafter discovered techniques. In various embodiments, the fatty acid alkyl ester is prepared by blending fatty acid alkyl esters of varying degrees of saturation to achieve the desired combinations described above. For instance, a fatty acid alkyl ester can be prepared by combining a mono-unsaturated fatty acid alkyl ester (e.g., 30 wt %), a di-unsaturated fatty acid alkyl ester (e.g., 60 wt %), a polyunsaturated fatty acid alkyl ester (e.g., 3 wt %), and a saturated fatty acid alkyl ester (e.g., 7 wt %). Thereafter, the combined product can be blended employing conventional techniques. For example, the components in desired amounts could be mixed at room temperature or elevated temperature in a reactor/vessel and mixed with continuous agitation until a homogeneous mass is obtained. Alternatively, any other method that results in a substantially uniform and homogeneous mass could be adopted. In such embodiments, commercially available fatty acid alkyl esters can be combined to form the fatty acid alkyl ester starting material. For example, methyl oleate, methyl linoleate, and methyl linoleate are available from TCI Chemicals, Tokyo, JP.

In other embodiments, the fatty acid alkyl ester can be prepared by genetically modifying the source of a natural oil to (e.g., sunflower, soybean, algae, bacteria) to produce triglyceride compositions having increased content of mono-unsaturated and di-unsaturated fatty acid chains. Subsequent esterification of such genetically modified compositions could result in fatty acid alkyl esters meeting the above description.

The above-described fatty acid alkyl ester is epoxidized to thereby form epoxidized fatty acid alkyl ester ("eFAAE"). Epoxidation can be performed according to any known or hereafter discovered epoxidation techniques in the art. In an embodiment, the fatty acid alkyl ester is epoxidized via contact with an acid and an aqueous peroxide solution to thereby produce an epoxidized reaction mixture comprising epoxidized fatty acid alkyl ester, residual acid, residual peroxide, and water. Suitable peroxides for use in epoxidizing the fatty acid alkyl ester include aqueous solutions of hydrogen peroxide, peroxycarboxylic acids, alkyl hydroperoxides, and tertiary hydroperoxides. In an embodiment, the peroxide employed is an aqueous solution of hydrogen peroxide.

Suitable acids for use in epoxidizing the fatty acid alkyl ester include carboxylic acids, such as formic acid and acetic acid; and peroxycarboxylic acids, such as performic acid and peracetic acid. In an embodiment, a peroxycarboxylic acid is employed, acting as both the acid and the peroxide. Catalysts such as mineral acids (e.g.; sulfuric acid) and heterogeneous acid resins (e.g., Amberlite™ IR 120H, available from Rohm & Haas) may optionally be employed in the presence of the acid. In an embodiment, the acid employed for epoxidation is formic acid.

Following epoxidation, the residual acid, peroxide, and water is removed from the epoxidized reaction mixture via layer separation and neutralization. Layer separation involves separation of an aqueous layer, which contains water, acids, peroxide, and possible traces of oil and esters, from an organic layer containing the eFAAE. To accomplish layer separation, the reaction mixture is allowed to settle and separate into two layers by density difference, and the bottom aqueous layer is disposed of while the top organic layer is processed further to obtain the desired product.

Following layer separation, the residual acid can be neutralized, such as by contact with a sodium/bicarbonate solution. Thereafter, the organic layer can be washed one or more times with water. In an embodiment, the organic layer is washed repeatedly until it is neutral (having a pH of about 7). Thereafter, the washed mixture can be subjected to layer separation again, followed by vacuum distillation of the top organic layer to remove residual water.

The compositions of this invention can alternatively be prepared by blending the appropriate epoxidized fatty acid alkyl esters to achieve the desired compositions.

The resulting eFAAE can exhibit a solubility in polyvinyl chloride ("PVC") of at least 30, at least 40, at least 50, at least 60, at least 70, at least 80, at least 90, at least 100, at least 110, at least 120, at least 130, or at least 140 grams per 100 grams of PVC at 80° C. The solubility in PVC in such embodiments can have a practical upper limit of 500 grams per 100 grams of PVC at 80° C. Solubility in PVC is determined according to American Society for Testing and Materials ("ASTM") method D 3367-98. In addition, the epoxidized fatty acid alkyl ester can have an oxirane oxygen value of at least 3.5, or in the range of from 4.0 to 7.8, as determined by American Oil Chemists' Society ("AOCS") method Cd 9-57. In addition, the epoxidized fatty acid alkyl ester can have an iodine value less than 10 g/100 g, or in the range of from 1.0 to 8.0, as determined by American Oil Chemists' Society ("AOCS") method Cd 1-25. Furthermore, the epoxidized fatty acid alkyl ester can exhibit a water solubility of less than 3 wt %, less than 2.5 wt %, less than 2 wt %, less than 1.5 wt %, or less than 1 wt %. In such embodiments, the epoxidized fatty acid alkyl ester can exhibit a water solubility as low as 0.7 wt %, 0.6 wt %, or 0.5 wt %. Water solubility of the epoxidized fatty acid alkyl ester is determined according to the procedures described in the Test Methods section, below.

In an embodiment, the plasticizer can further comprise an epoxidized natural oil ("eNO"). A "natural oil," as used herein, is an oil composed of fatty acid triglycerides and derived from a microbe (algae, bacteria), a plant/vegetable, and/or a seed. In an embodiment, natural oils include genetically-modified natural oils. In various embodiments, the natural oil excludes petroleum-derived oil. Non-limiting examples of suitable natural oils include beef tallow oil, canola oil, castor oil, corn oil, fish oil, linseed oil, palm oil, rapeseed oil, safflower oil, soybean oil, sunflower oil, tall oil, tung oil, and any combination of two or more thereof.

The term "epoxidized natural oil," as used herein, is a natural oil having at least one fatty acid moiety that contains at least one epoxide group. Epoxidation may be performed as described above, typically by way of reaction of the natural oil with a peroxide, a percarboxylic acid, and/or other peroxy compounds, often in the presence of an acid or base catalyst.

Non-limiting examples of suitable eNOs include epoxidized algae oil, epoxidized beef tallow oil, epoxidized canola oil, epoxidized castor oil, epoxidized corn oil, epoxidized fish oil, epoxidized linseed oil, epoxidized palm oil, epoxidized rapeseed oil, epoxidized safflower oil, epoxidized soybean oil, epoxidized sunflower oil, epoxidized tall oil, epoxidized tung oil, and any combination of two or more thereof.

In an embodiment, the epoxidized natural oil is an epoxidized soybean oil ("eSO").

Examples of suitable commercially available epoxidized natural oils include PLAS-CHEK™ epoxidized soybean oil, available from Ferro Corp., Mayfield Heights, Ohio, USA; VIKOFLEX™ 7170 epoxidized soybean oil and VIKOFLEX™ 7190 epoxidized linseed oil, both available from Arkema Inc., Philadelphia, Pa., USA.

In various embodiments, the eFAAE constitutes the entirety of the plasticizer. In other embodiments, when more than one component is present in the plasticizer, the plasticizer can comprise the eFAAE in an amount ranging from 20 to 80 wt %, 30 to 70 wt %, 40 to 60 wt %, or 50 wt % based on the entire plasticizer weight. The remainder can be eNO. In various embodiments, the plasticizer is a 50:50 blend by weight of eFAAE and eNO (e.g., eSO). In various embodiments, the plasticizer is free or substantially free of phthalates.

Polymeric Composition

The present disclosure provides a polymeric composition comprising a polymeric resin and the above-described plasticizer. In various embodiments, the polymeric composition is free or substantially free of phthalates.

Non-limiting examples of suitable polymeric resins include polysulfides, polyurethanes, acrylics, epichlorohydrins, nitrile rubber, chlorosulfonated polyethylene, chlorinated polyethylene, polychloroprene, styrene butadiene rubber, natural rubber, synthetic rubber, ethylene-propylene-diene monomer rubber, propylene-based polymers, ethylene-based polymers, and vinyl chloride resins. The term "propylene-based polymer" denotes a polymer comprising a majority weight percent polymerized propylene monomer (based on the total amount of polymerizable monomers) and optionally at least one polymerized comonomer. The term "ethylene-based polymer" denotes a polymer comprising a majority weight percent polymerized ethylene monomer (based on the total weight of polymerizable monomers) and optionally at least one polymerized comonomer.

The term "vinyl chloride resin" denotes a vinyl chloride polymer, such as polyvinyl chloride ("PVC"), or a vinyl chloride copolymer, such as vinyl chloride/vinyl acetate copolymer, vinyl chloride/vinylidene chloride copolymer, vinyl chloride/ethylene copolymer, or a copolymer prepared by grafting vinyl chloride onto ethylene/vinyl acetate copolymer. The vinyl chloride resin can also include a polymer blend of the above-mentioned vinyl chloride polymer or vinyl chloride copolymer with other miscible or compatible polymers including, but not limited to, chlorinated polyethylene, thermoplastic polyurethane, olefin polymers such as a methacryl polymer, or acrylonitrile-butadiene-styrene polymer.

In an embodiment, the vinyl chloride resin is PVC.

In an embodiment, the polymeric composition comprises the polymeric resin in an amount ranging from 20 to 90 wt %, from 30 to 85 wt %, or from 40 to 80 wt %, based on the entire polymeric composition weight. In various embodiments, the polymeric composition comprises the above-described plasticizer in an amount ranging from 10 to 80 wt %, from 15 to 70 wt %, or from 20 to 60 wt %, based on the entire polymeric composition weight.

In various embodiments, the polymeric resin (such as PVC) has a solution temperature in the above-described plasticizer of less than 180° C., less than 170° C., or less than 160° C., as determined by Deutsches Institut für Normung ("DIN") standard method 53 408.

Additives

The polymeric composition may include one or more of the following optional additives: a filler, a flame retardant, a heat stabilizer, an anti-drip agent, a colorant, a lubricant, a low molecular weight polyethylene, a hindered amine light stabilizer, a UV light absorber, a curing agent, a booster, a retardant, a processing aid, a coupling agent, an antistatic agent, a nucleating agent, a slip agent, a viscosity control agent, a tackifier, an anti-blocking agent, a surfactant, an extender oil, an acid scavenger, a metal deactivator, and any combination thereof.

In an embodiment, the polymeric composition comprises a heat stabilizer. Examples of suitable heat stabilizers include lead-free metal soaps, lead stabilizers, organic heat stabilizers, epoxides, salts of monocarboxylic acids, phenolic antioxidants, organic phosphites, and beta-diketones. In an embodiment, the heat stabilizer employed is a lead-free mixed metal soap. The term "metal soap" denotes a salt of an acid with a metal. Metal soaps suitable for use include zinc salts of fatty acids (e.g., zinc stearate), calcium salts of fatty acids, barium salts of fatty acids, magnesium salts of fatty acids, tin salts of fatty acids, and mixtures of two or more thereof. Heat stabilizers can be present in the polymeric composition in an amount ranging from 0.2 to 10 wt %, from 0.4 to 7 wt %, or from 0.6 to 5 wt %, based on the entire polymeric composition weight.

In an embodiment, the polymeric composition includes PVC, the present plasticizer, a filler (e.g., calcium carbonate, clays, silica, and any combination thereof), one or more metal soap stabilizers, a phenolic or related antioxidant, and a processing aid.

Coated Conductor

The present disclosure provides a coated conductor. The coated conductor includes a conductor and a coating on the conductor, the coating being at least partially being formed from the polymeric composition described above.

A "conductor," as used herein, is one or more wire(s) or fiber(s) for conducting heat, light, and/or electricity. The conductor may be a single-wire/fiber or a multi-wire/fiber and may be in strand form or in tubular form. "Wire" means a single strand of conductive metal or a single strand of optical fiber. Non-limiting examples of suitable conductors include metals such as silver, gold, copper, carbon, and aluminum. The conductor may also be optical fiber made from either glass or plastic.

The coated conductor may be flexible, semi-rigid, or rigid. The coating (also referred to as a "jacket," "sheath," or "insulation") can be located either directly on the conductor or on another layer that surrounds the conductor.

In an embodiment, the coated conductor is a cable. "Cable" and "power cable" mean at least one wire or optical fiber within a sheath. Typically, a cable is two or more wires or optical fibers bound together, typically in a common insulation covering and/or protective jacket. The individual wires or fibers inside the sheath may be bare, covered or insulated. Combination cables may contain both electrical wires and optical fibers. The cable can be designed for low, medium, and/or high voltage applications. Typical cable designs are illustrated in U.S. Pat. Nos. 5,246,783, 6,496, 629 and 6,714,707.

Articles of Manufacture

In addition to the coated conductors described above, articles of manufacture can be prepared that comprise the above-described polymeric compositions. Such articles of manufacture can include those designed for use in the medical or food industries, particularly those articles that may frequently come into contact with water and where water-leachable compounds are a concern. Exemplary articles of manufacture include blood bags, intravenous bags, saline solution bags, syringes, intravenous tubing, nasogastric tubing, catheter tubing, drainage tubing, examination gloves, oxygen masks, orthodontic retainers, artificial skin, and food packaging (e.g., packaging for various beverages, meats, and frozen vegetables).

Test Methods

Oxirane Oxygen Value

Determine oxirane oxygen value according to AOCS Cd 9-57.

Iodine Value

Determine iodine value according to AOCS Cd 1-25.

Solubility in PVC

Measure solubility in PVC according to ASTM D 3367-98.

Test parameters, such as the design of centrifuge tubes, soak temperature, soak time, drainage of plasticizer, and centrifuge speed to remove excess plasticizer, are optimized to be able to capture differences in plasticizer absorption and solubilities of different plasticizers in PVC. Centrifuge tubes with a 0.8 mm diameter hole at the bottom are used for the test. The hole is covered with 0.1 g cotton. 1 g PVC (preheated at 80° C. for 1 hour) and 4 g plasticizer (preheated at 80° C. for 1 hour) are weighed in the centrifuge tubes on top of the cotton. The centrifuge tubes (containing cotton, PVC and plasticizer) are inserted in sheaths and the assembly is soaked at 80° C. for 4 hours. During the soak time, the plasticizer molecules wet the cell walls of PVC particles and penetrate through it due to its porosity. Once inside, the molecules start filling the void space. After the void space is completely filled with plasticizer, the PVC primary particles start absorbing the plasticizer. This absorption is relatively slow and continues until the primary particles reach saturation limit. It is therefore important to optimize the PVC/plasticizer soaking temperature and time. Following this, the tubes are centrifuged at 7000 rpm for 1 hour to remove the excess plasticizer which flows out through the cotton and 0.8 mm diameter hole and is collected in the outer sheath. The plasticizer absorbed by PVC is measured from the weight gain of PVC (after accounting for weight gain due to plasticizer absorbed by cotton). The equilibrium plasticizer solubility is calculated by subtracting the void volume (found to be equal to amount of acetylated castor wax absorbed by PVC, see PCT Published Application WO/2011/041380) from the plasticizer absorption.

Solution Temperature

Determine solution temperature in accordance with Deutsches Institut für Normung ("DIN") 53408. Important test parameters such as the PVC/plasticizer amount and heating rate are optimized to be able to capture differences in solution temperature of different plasticizers in PVC. 0.6 g PVC is accurately weighed in a 20-mL glass vial and 15 mL of plasticizer is added to the PVC. The contents of the glass vial are stirred using a magnetic stirrer and heated using an oil bath at 1° C./min. A thermometer is used to record the temperature of the PVC/plasticizer mixture which is illuminated with a flash-light. When PVC is mixed with a plasticizer, a milky solution is generally obtained. As the temperature of the PVC/plasticizer mixture is raised, the PVC starts to imbibe the plasticizer and becomes translucent. As the temperature is raised further, the PVC particles swell and lose their shape forming a gel. At the solution temperature, a clear solution is obtained.

Water Solubility 20 mL of plasticizer is taken in a beaker and mixed with equal volume of distilled water. The mixture is stirred vigorously at room temperature and allowed to settle in a separating funnel. The mixture forms an emulsion which takes approximately 24 hours to form separate layers of organic and aqueous phases. After 48 hours, the two layers are separated. The aqueous layer is drained and the organic layer containing plasticizer and some water is recovered. The organic layer contains water in dissolved form as well as in the fine emulsion form. This layer is centrifuged at 7000 rpm for one hour. This step separates water trapped in the plasticizer in dispersed form. The plasticizer is further analyzed for water content with the help of wet chemistry methods. Carl Fischer titration method is used to determine the water content in plasticizer.

Infrared Spectroscopy

Fourier Transform infrared ("FTIR") spectroscopy is used for the qualitative finding of the components present in the samples. FTIR Instrument: Thermo Nicolet 6700 FTIR with Smart Orbit Diamond Crystal ATR accessory. Wavelength range: 4000 to 400 $cm^{-1}$; Resolution: 4.0; Background collection: air background collected before each sample; Number of scans: 150. Attenuated Total Reflectance ("ATR") is used to study the films in the reflectance mode. A resolution of 4 $cm^{-1}$ and 100 sample scans are used.

EXAMPLES

Example 1—Comparison of Methyl Oleate- and Methyl Linoleate- to Methyl Linolenate-Based Plasticizers Prepare two samples (S1 and S2) and four comparative samples (CS1-CS4) as follows.

Preparation of Sample 1

S1 is an epoxidized methyl oleate. Prepare S1 by epoxidizing methyl oleate (~90% GC purity synthesized by esterification of oleic acid with methanol in presence of acid catalyst at reflux temperature of alcohol with 6 hours of reaction) using hydrogen peroxide ("$H_2O_2$"; 30 wt %, available from RANKEM) and formic acid ("FA", 90%, available from RANKEM) at 40° C. for 11 hours using a mole ratio of 1:2:0.5 of carbon-carbon double bonds in the methyl oleate ("C=C")-to-$H_2O_2$-to-FA. The reaction is carried out in a glass reactor with continuous stirring and immersed in an oil bath. The reaction temperature is achieved and maintained by controlling bath temperature by way of an electrically heated hot plate. The mixing is ensured during reaction using an overhead stirrer. After charging methyl oleate (50 g) and formic acid (4.3 g) in the required amount, a calculated amount of an aqueous solution of $H_2O_2$ (38.3 gm) is added in the reactor with the help of a pump over a period of 1 hour. The pump flow rate (35 mL/hr) is adjusted such as the total addition time is 1 hour. Monitor the oxirane oxygen value using wet chemistry methods mentioned above (i.e., AOCS Cd 9-57) throughout the epoxidation reaction. The theoretical oxirane oxygen value for methyl oleate is 5.1. Analyze the resulting sample according to the Test Methods provided above. Results are provided in Table 1, below.

Preparation of Sample 2

S2 is an epoxidized methyl linoleate. Prepare S2 by epoxidizing 50 g of methyl linoleate (95% purity obtained from TCI chemicals) using the method described above for preparation of S1, with the following exceptions: the $H_2O_2$ is a 50 wt % solution (46.3 g) in water (available from Fischer Scientific) and formic acid is used in an amount of 4.35 g for S2. The theoretical oxirane oxygen value for methyl linoleate is 9.8. Analyze the resulting sample according to the Test Methods provided above. Results are provided in Table 1, below.

Comparative Sample 1

CS1 is an epoxidized methyl linolenate. Prepare CS1 by epoxidizing 50 g of methyl linolenate (90% purity, available from TCI chemicals) using the method described above for preparation of S1, with the following exceptions: (a) 3.2 g acetic acid ("AA", glacial acetic acid >99% purity, available from S.d.fine-chem Limited) is used in place of formic acid; (b) epoxidation is performed at 65° C. for 5 hours; (c) C═C:$H_2O_2$:AA is 1:2:0.3; (d) $H_2O_2$ (69.9 g of 50 wt % solution) addition performed over 4 hours; and (e) a catalytic amount of sulphuric acid (0.5 mL) is employed at 2 weight percent based on the C═C concentration. The theoretical oxirane oxygen value for methyl linolenate is 14. Analyze the resulting sample according to the Test Methods provided above. Results are provided in Table 1, below.

Comparative Sample 2

CS2 is an epoxidized methyl linolenate. Prepare CS2 by epoxidizing a methyl linolenate using the method described above for preparation of S1, with the following exception: $H_2O_2$ addition is performed over a period of 3 hours. The starting methyl linolenate is the same as in CS1. Analyze the resulting sample according to the Test Methods provided above. Results are provided in Table 1, below.

Comparative Samples 3 and 4

CS3 and CS4 are epoxidized methyl linolenates. Prepare CS3 and CS4 by epoxidizing a methyl linolenate using the method described above for preparation of S1, with the following exceptions: (a) epoxidation is performed for a total of 9 hours reaction time; (b) $H_2O_2$ addition is performed over a period of 1.5 hours; (c) add $H_2O_2$ at ambient temperature (24-25° C.), then raise the reaction temperature to 40° C. for remainder of the reaction. The starting methyl linolenate is the same as in CS1. Analyze the resulting sample according to the Test Methods provided above. Results are provided in Table 1, below.

Analysis

The results from analyses of S1, S2, and CS1-4 are provided in Table 1, below. Note that the equilibrium solubility is determined only for samples which have oxirane oxygen values close to theoretical values (S1, S2, and CS4). Also, the water uptake is measured only for epoxidized methyl oleate (S1) and epoxidized methyl linolenate having an oxirane oxygen value of 6 (CS2).

TABLE 1

Properties of single chain epoxidized FAME derivatives

| | Sample: | | | | | |
|---|---|---|---|---|---|---|
| | S1 | S2 | CS1 | CS2 | CS3 | CS4 |
| Starting material | Methyl oleate | Methyl linoleate | Methyl linolenate | Methyl linolenate | Methyl linolenate | Methyl linolenate |
| Theoretical maximum oxirane oxygen value | 5.2 | 9.8 | 14.1 | 14.1 | 14.1 | 14.1 |
| Final oxirane oxygen value | 4.68 | 8.3 | 0.28 | 6.0 | 8.97 | 9.28 |
| Interim oxirane oxygen value | 3.4 (after 7 hours) | 7.8 (after 7 hours) | N/A | 7.8 (after 7 hours) | 8.87 (after 9 hours) | 7.0 (after 7 hours) |
| Iodine value | 7.4 | 2.8 | 69 | 8.5 | 63.66 | 37.32 |
| Oxirane conversion (%) | 90 | 85 | 2 | 43 | 64 | 66 |
| Conversion based on iodine value (%) | 91.34 | 98.37 | 74.44 | 96.73 | 75.5 | 78.32 |
| Solution temperature (° C.) | 114 | 88 | — | 124 | 98 | 98 |
| Solubility in PVC (g/100 g PVC) | 73 | 244 | — | N/A | N/A | 223.6 |
| Water solubility (%) | 0.68 | — | — | 4.77 | — | — |

Table 1 shows that epoxidation of methyl oleate (S1) and linoleate (S2) can be carried out with ease and oxirane oxygen values close to theoretical values can be obtained. No degradation of oxirane oxygen ring during the reaction is observed. In contrast, epoxidation of methyl linolenate results in ring opening of oxirane ring, as evidenced by the low oxirane oxygen conversion values and high exothermicity during the reaction. The highest oxirane oxygen value obtained with methyl linolenate under these reaction conditions was 9.28 (CS4), compared to a theoretical maximum of 14.1.

These experimental results indicate that epoxidation of oleate and linoleate is relatively easy and theoretical oxirane oxygen values are achievable, as compared to linolenate where the epoxidation low percent oxirane oxygen yield is obtained with significant ring opening of the oxirane ring, which leads to hydroxyl compounds. The IR spectra (FIG. 1) for S1, S2, CS1, and CS2 indicate the presence of OH groups in only the epoxidized methyl linolenate with oxirane oxygen value of 6 (CS2).

It should be noted that, in the case of CS1, using the mole ratio of 1:2:0.3 of C═C:$H_2O_2$:AA with 30 wt % $H_2O_2$ solution and carrying out the reaction at 65° C., the oxirane oxygen value is only 0.28 at the end of 5 hours. Changing the mole ratios to 1:2:0.5 and using formic acid at 40° C. (CS2) the final oxirane oxygen initially increases to 7.8 at the end of 7 hours of reaction, and then decreases to 6 at the end of the reaction. Exothermicity is observed in the both reactions, although it is less at 40° C. (CS2). With CS3 and CS4, exothermicity is controlled by slow addition of hydrogen peroxide over a period of 1.5 hours at ambient temperature (24-25° C.) and then continuing the reaction at 40° C. This results in appreciably higher oxirane oxygen yields (albeit far below the theoretical value), but the iodine values are unacceptably high.

Example 2—Comparison of High Oleate and Linoleate eFAME to Soy eFAME

Samples 3 and 4

Prepare two samples (S3 and S4) having high methyl oleate (C18:1) and methyl linoleate (C18:2) content, and epoxidize them. S3 has a combined C18:1 and C18:2 content of about 85 wt %, and S4 has a combined C18:1 and C18:2 content of about 90 wt %, as detailed in Table 2, below. The remainder of S3 and S4 is made up of methyl linolenate (C18:3) and methyl stearate (C18:0).

Prepare S3 and S4 by initially mixing epoxidized methyl linoleate and epoxidized methyl linolenate prepared as described in the above examples with epoxidized soy FAME (e-FAME) prepared as described in Comparative Sample 5, below. The desired composition for S3 and S4 is achieved by mixing these components in appropriate proportions in a stirred tank reactor until a uniform, homogeneous mass is obtained. Thereafter, analyze the samples according to the Test Methods described above. The results are provided in Table 3, below.

Comparative Sample 5

Prepare Comparative Sample 5 (CS5) by epoxidizing soybean oil (available from Gemini Cargill) according to the epoxidation procedure described above for S2 to obtain epoxidized soybean oil ("eSO"). Transesterify 100 g of eSO using 20 g of methanol (>99% purity obtained from S.d.finechem, Limited) in the presence of 4 g of sodium methoxide (25% solution in methanol, available from Sigma Aldrich) catalyst at 60° C. for 3 hours. Following transesterification, analyze CS5 according to the Test Methods described above. The results are provided in Table 3, below.

TABLE 2

Composition of S3, S4, and CS5

| | Sample: | | |
|---|---|---|---|
| | S3 | S4 | CS5 |
| C18:1 content (wt %) | 27.03 | 28.55 | 24.37 |
| C18:2 content (wt %) | 57.75 | 61.30 | 55.33 |
| Combined C18: 1 + C18:2 (wt %) | 84.78 | 89.85 | 79.71 |

TABLE 2-continued

Composition of S3, S4, and CS5

| | Sample: | | |
|---|---|---|---|
| | S3 | S4 | CS5 |
| C18:3 content (wt %) | 3.92 | 2.62 | 5.23 |
| C18:0 content (wt %) | 11.30 | 7.53 | 15.06 |

The results from analyses of S3, S4, and CS5 are provided in Table 3, below:

TABLE 3

Properties of blended epoxidized FAME

| | Sample: | | |
|---|---|---|---|
| | S3 | S4 | CS5 |
| Oxirane oxygen value (measured) | 6.77 | 6.83 | 6.73 |
| Oxirane oxygen value (theoretical) | 7.41 | 7.72 | 7.15 |
| Oxirane conversion (%) | 91.364 | 88.384 | 94.015 |
| Iodine value | 4.21 | 3.33 | 2.06 |
| Solubility in PVC (g/100 g PVC) | 127.9 | 140.9 | 96.1 |
| Water solubility (wt %) | 1.0401 | 0.9643 | 1.0400 |
| Solution Temperature (° C.) | 116 | 110 | 100 |

As seen in Table 3, Samples 3 and 4 provide increased solubility in PVC, indicating enhanced plasticizer performance. Additionally, lower water uptake by S4 indicates lower hydroxyl content. Lower water absorption can be beneficial for wet electrical insulation resistance.

Example 3—Comparison of Varied Ester Alkyl Chain Lengths

Prepare five epoxidized alkyl oleate samples (S5-S9) as follows using the epoxidation procedure described above for the preparation of S2. S5 is exactly same as S1 and re-considered here for comparison. The starting material for S6 is 1-propyl oleate, synthesized by esterification of oleic acid with 1-propanol in presence of acid catalyst at reflux temperature of alcohol with 6 hours of reaction. The starting material for S7 is 2-propyl oleate, synthesized by esterification of oleic acid with 2-propanol in presence of acid catalyst at reflux temperature of alcohol with 6 hours of reaction. The starting material for S8 is 1-butyl oleate, synthesized by esterification of oleic acid with 1-butanol in presence of acid catalyst at reflux temperature of alcohol with 6 hours of reaction. The starting material for S9 is isobutyl oleate, synthesized by esterification of oleic acid with isobutanol in presence of acid catalyst at reflux temperature of alcohol with 6 hours of reaction. Following epoxidation, analyze each of the samples according to the Test Methods provided above. Results are provided in Table 4, below:

TABLE 4

Properties of epoxidized fatty acid alkyl esters

| | Sample: | | | | |
|---|---|---|---|---|---|
| | S5 | S6 | S7 | S8 | S9 |
| Starting Material | Methyl Oleate | 1-Propyl Oleate | 2-Propyl Oleate | 1-Butyl Oleate | Isobutyl Oleate |
| Oxirane oxygen value | 4.68 | 5.13 | 5.16 | 4.69 | 4.97 |
| Iodine value | 7.4 | 0 | 1.7 | 2.04 | 2.20 |
| Oxirane conversion (%) | 91 | ~100 | ~100 | ~100 | ~100 |
| Solubility in PVC (g/100 g PVC) | 73.2 | 66.5 | 34.1 | 54.9 | 56.9 |
| Solution Temperature (° C.) | 114 | 116 | 134 | 120 | 118 |

As seen in Table 4, epoxidized alkyl oleate samples having longer ester alkyl chain lengths (S6-S9) can provide comparable oxirane conversion to epoxidized methyl oleate (S5). In fact, a higher percentage of oxirane conversion is seen in each of S6-S9 as compared to S5. This indicates relatively lower hydroxyl content, which in turn will result in decreased water absorption and, thus, improved wet electrical insulation resistance. The eFAAE of Table 4 also exhibit sufficient solubility of at least 30 grams per 100 grams of PVC at 80° C.

Example 4—Model Comparison of Varied Fatty Acid Chain Lengths

Tables 5 and 6, below, present model data comparing epoxidized methyl esters of various fatty acids having different chain lengths and numbers of unsaturation. Geometry optimization of these molecular structures is performed with TURBOMOLE version 5.0 (available from CSOMOlogic GmbH & Co. KG) using TZVP basis set and BP86 exchange correlation functional within the density functional theory formalism. Along with the .cosmo files generated via TURBOMOLE, BP_TZVP_C21_0111.ctd parameterization is utilized in COSMOtherm version C21_0111_a (available from COSMOlogic GmbH & Co. KG). To calculate solubility of epoxidized FAME in PVC at 90° C., at first the infinite dilution activity coefficient, $\gamma^\circ$, is calculated using COSMOtherm. The PVC is modeled as a polymer within the metafile approach available within COMOtherm, where the hydrogen bond and the combinatorial contribution to the chemical potential are neglected. The following equation is used to calculate the solubility (g/100 g):

Solubility=53430.50*EXP(−(7.07*$\gamma^\circ$))+86.85*EXP(−(1.23*$\gamma^\circ$))

The data for the water molecule is used as available within COSMOtherm. Solubility of water in epoxidized FAME is calculated in the pure phase of each of the epoxidized FAME listed in Table 6 using COSMOtherm at 25° C.

TABLE 5

Comparison of model predictions with experimental solubility of epoxidized alkyl oleate in PVC

| Sample | Alkyl Group | Solubility in PVC (from the Model) (g/100 g PVC) | Solubility in PVC (from Table 4) (g/100 g PVC) |
|---|---|---|---|
| S5 | Methyl | 86.9 | 73.2 |
| S6 | 1-Propyl | 46.1 | 66.5 |
| S8 | 1-Butyl | 37.2 | 54.9 |

As can be seen from Table 5, model calculations show that, for higher alkyl groups, the solubility of epoxidized alkyl ester of oleate decreases in PVC as compared to epoxidized methyl ester of oleate. This is also seen from the experimentally measured solubility in PVC as listed in Table 4. The model-determined solubilities at 80° C., of the eFAAE of Table 5, are also at least 30 grams per 100 grams of PVC.

TABLE 6

Model comparison of epoxidized FAME

| Model Sample No. | Carbon Chain Length | Number of epoxy oxygens per chain | Solubility in PVC (g/100 g PVC) | Water solubility (wt %) |
|---|---|---|---|---|
| MS1 | 12 | 1 | 233.78 | 2.3116 |
| MS2 | 14 | 1 | 162.83 | 1.4949 |
| MS3 | 16 | 1 | 105.46 | 1.0903 |
| MS4 | 16 | 2 | 283.30 | 1.6104 |
| MS5 | 22 | 1 | 30.01 | 0.5781 |
| MS6 | 24 | 1 | 59.03 | 0.8426 |

As seen in Table 6, epoxidized fatty acids having from 12 to 16 carbon atoms and 1 or 2 epoxy oxygen atoms provide comparable or better performance as epoxidized oleates and linoleates with respect to PVC solubility (compare S1-S4, above). Decreased water absorption will lead to improved wet electrical insulation resistance. It should be noted that the lower solubility in PVC of MS5 and MS6 is likely due to the increased number of methylene groups in the carbon chain, which increases the hydrophobic content of the molecule and hence lowers compatibility of the plasticizer with PVC.

Example 5—Model Comparison of Varied Ester Alkyl Chain Lengths and Varied Fatty Acid Chain Lengths Table 7, below, presents model data comparing epoxidized alkyl esters of various fatty acids having varied alkyl chain lengths, varied fatty acid chain lengths, and varied numbers of unsaturation. Model data is generated as described above in Example 4.

TABLE 7

Model comparison of epoxidized FAAE

| Model Sample No. | Alkyl Chain Length | Fatty Acid Chain Length | Number of epoxy oxygens per chain | Solubility in PVC (g/100 g PVC) |
|---|---|---|---|---|
| MS7 | propyl | 12 | 1 | 208.53 |
| MS8 | propyl | 14 | 1 | 128.44 |
| MS9 | propyl | 16 | 1 | 63.79 |
| MS10 | propyl | 16 | 2 | 372.12 |
| MS11 | butyl | 12 | 1 | 191.58 |

TABLE 7-continued

Model comparison of epoxidized FAAE

| Model Sample No. | Alkyl Chain Length | Fatty Acid Chain Length | Number of epoxy oxygens per chain | Solubility in PVC (g/100 g PVC) |
|---|---|---|---|---|
| MS12 | butyl | 14 | 1 | 99.01 |
| MS13 | butyl | 16 | 1 | 50.39 |
| MS14 | butyl | 16 | 2 | 328.70 |

As seen in Table 7, epoxidized fatty acids having from 12 to 16 carbon atoms with various alkyl chain lengths and 1 or 2 epoxy oxygen atoms provide comparable or better performance as epoxidized oleates and linoleates with respect to PVC solubility (compare S1-S4, above).

The invention claimed is:

1. A process for making a plasticizer, said process comprising:
   epoxidizing a fatty acid alkyl ester, thereby producing an epoxidized fatty acid alkyl ester; and
   combining an epoxidized natural oil with at least a portion of said epoxidized fatty acid alkyl ester,
   wherein said fatty acid alkyl ester comprises mono-unsaturated fatty acid alkyl ester molecules and di-unsaturated fatty acid alkyl ester molecules in a combined amount of at least 85 weight percent, based on the total weight of said fatty acid alkyl ester.

2. The process of claim 1, wherein said fatty acid alkyl ester comprises fatty acid alkyl ester molecules having three or more carbon-carbon double bounds in an amount of less than 5 weight percent, based on the total weight of said fatty acid alkyl ester.

3. The process of claim 1, wherein said fatty acid alkyl ester comprises saturated fatty acid alkyl ester molecules in an amount of less than 14 weight percent, based on the total weight of said fatty acid alkyl ester.

4. The process of claim 1, wherein said fatty acid alkyl ester is fatty acid methyl ester, wherein said mono-unsaturated fatty acid alkyl ester molecules are methyl oleates, wherein said di-unsaturated fatty acid alkyl ester molecules are methyl linoleates.

5. The process of claim 1, wherein said epoxidized fatty acid alkyl ester exhibits a solubility in polyvinyl chloride ("PVC") of at least 30 grams per 100 grams of PVC at 80° C., wherein said epoxidized fatty acid alkyl ester has an oxirane oxygen value of at least 3.5, wherein said epoxidized fatty acid alkyl ester has a water solubility of less than 3 wt %.

6. A polymeric composition comprising a polymeric resin and said epoxidized fatty acid alkyl ester produced by the process of claim 1.

7. The polymeric composition of claim 6, wherein said polymeric resin is PVC.

8. An article of manufacture comprising the polymeric composition of claim 6.

9. The article of manufacture of claim 8, wherein said article of manufacture is selected from the group consisting of coated conductors, blood bags, intravenous bags, saline solution bags, syringes, intravenous tubing, nasogastric tubing, catheter tubing, drainage tubing, examination gloves, oxygen masks, orthodontic retainers, artificial skin, and food packaging.

* * * * *